United States Patent [19]

Rogers et al.

[11] Patent Number: 4,728,657

[45] Date of Patent: Mar. 1, 1988

[54] ARYL(ARYLOXY OR ARYLTHIO)AZOLOMETHANES

[75] Inventors: Richard B. Rogers, Concord; Maria P. Herrero, Berkeley, both of Calif.

[73] Assignee: The Dow Chemical Company, Midland, Mich.

[21] Appl. No.: 897,572

[22] Filed: Aug. 18, 1986

Related U.S. Application Data

[60] Division of Ser. No. 653,399, Sep. 24, 1984, Pat. No. 4,636,514, which is a continuation of Ser. No. 407,852, Aug. 13, 1982, abandoned.

[51] Int. Cl.$^4$ .................. C07D 409/14; A61K 31/345
[52] U.S. Cl. ................................. 514/340; 514/341; 71/92; 546/276; 546/278
[58] Field of Search ....................... 546/276, 278, 279; 514/340, 341; 71/92

[56] References Cited

U.S. PATENT DOCUMENTS

| | | | |
|---|---|---|---|
| 3,709,901 | 1/1973 | Draber et al. | 548/336 |
| 3,755,345 | 8/1973 | Regel et al. | 548/262 |
| 3,870,726 | 3/1975 | Jager et al. | 548/335 |
| 4,062,959 | 12/1977 | Draber et al. | 514/252 |

FOREIGN PATENT DOCUMENTS 000752 2/1979 European Pat. Off.

*Primary Examiner*—Jane T. Fan
*Attorney, Agent, or Firm*—S. Preston Jones; Ronald G. Brookens

[57] ABSTRACT

Disclosed are aryl(aryloxy or arylthio) azolomethanes, their preparation and their pesticidal and plant growth regulation uses.

4 Claims, No Drawings

ARYL(ARYLOXY OR ARYLTHIO)AZOLOMETHANES

This is a divisional of application Ser. No. 653,399, filed Sept. 24, 1984 now U.S. Pat. No. 4,636,514, issued Jan. 13, 1987, which is a continuation of Ser. No. 407,852, filed Aug. 13, 1982, now abandoned.

SUMMARY OF THE INVENTION

The present invention is directed to aryl(aryloxy or arylthio)azolomethanes corresponding to the formula

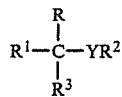

wherein

R represents hydrogen, phenyl, substituted phenyl, pyridyl or substituted pyridyl;

$R^1$ represents phenyl, substituted phenyl, pyridyl, or thienyl or substituted thienyl;

$R^2$ represents phenyl, substituted phenyl, or pyridyl or substituted pyridyl;

$R^3$ represents a 5-membered N-heterocyclic ring of the formula

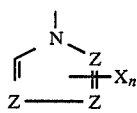

wherein each Z independently represents —CH or N and at least one of Z is N; X is $C_1$–$C_4$ alkyl, Br, Cl, F or I and n represents an integer of from 0 to 3 and Y is oxygen or sulfur.

In the present specification and claims, the terms "substituted phenyl", "substituted pyridyl" or "substituted thienyl" are employed to designate phenyl, pyridyl or thienyl groups which are substituted independently with from 1 to 2 to 3 bromo, chloro, fluoro or iodo, $C_1$–$C_4$ alkyl, $C_1$–$C_4$ alkoxy, $NO_2$, —CN or $CF_3$ groups. The substitutions can be the same or different. The terms "alkyl" and "alkoxy" as employed herein represent straight, branched chain or cyclic alkyl or alkoxy groups. It is to be noted that all substituent groups are sterically compatible with each other.

In the present specification and claims, the term "sterically compatible" is employed to designate X and Z substituent groups which are not affected by steric hindrance as defined in "The Condensed Chemical Dictionary", 7th edition, Reinhold Publishing Co., N.Y., page 893 (1966) which definition is as follows: "steric hindrance. A characteristic of molecular structure in which the molecules have a spatial arrangement of their atoms such that a given reaction with another molecule is prevented or retarded in rate."

Steric hindrance may be further defined as compounds having substituents whose physical bulk does not require confinement within volumes insufficient for the exercise of their normal behavior as discussed in "Organic Chemistry" D. J. Cram and G. Hammond, 2nd edition, McGraw-Hill Book Company, N.Y., page 215 (1964).

The aryl(aryloxy or arylthio)azolomethanes of the present invention possess excellent pesticidal properties and are very useful for the control of various fungal or insect pest. In addition various compounds have been found to have plant growth regulation activity (enhancement, stunting or killing).

The azolomethane compounds of the present invention ae crystalline solids or liquids which are sparingly soluble in water and which are soluble in most organic solvents.

The azolomethane compounds of the present invention can be prepared employing a variety of methods.

Method A

Substantially equimolar amounts of a dihalomethyl compound corresponding to the formula

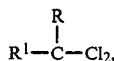

a phenol or thiophenol of the formula $HYR^2$ and a N-heterocyclic compound reactant $HR^3$ which corresponds to the formula

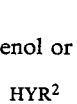

are reacted together in the presence of a solvent and a strong base. Representative of such bases include sodium hydride and potassium tertiary butoxide.

The reaction scheme is as follows:

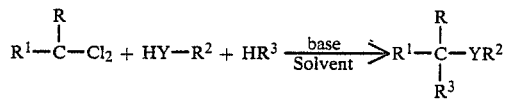

In the above R, $R^1$, $R^2$ and $R^3$ is a hereinabove defined and Me is alkali metal. No attempt has been made to present a balanced equation.

The reaction is conveniently carried out in an inert solvent which serves as a carrier medium. Representative inert solvents operable in the present invention include 1,2-dimethoxyethane, dimethylformamide (DMF), dimethylsulfoxide (DMSO) and the like. The amount of the reactants employed is not critical; ordinarily, essentially equimolar proportions of each reactant is employed. The reaction takes place smoothly at temperatures of from about 20° to about 200° C.; however, the reaction is preferably carried out at temperatures of from about 80° to about 130° C. While the reaction can be conducted over a wide range of pressures, no particular advantage ordinarily results from the use of sub- or super-atmospheric pressures and the reaction is therefore ordinarily carried out under ambient pressure conditions.

In carrying out the reaction, the reactants are contacted in any convenient fashion and the resulting reaction mixture is agitated in the reaction temperature range for a period of time sufficient to assure substantial completion of the reaction. The reaction time period, which varies from about 15 minutes to about 24 hours, is dependent upon the reaction temperature employed as well as the nature of the raw material reactants employed. Generally, the reaction time period ranges from about 1 to about 8 hours.

Following the completion of the reaction, the reaction mixture is cooled to room temperature, mixed with water and solvent extracted. The extract is washed with a mild aqueous basic solution, dried and the carrier medium removed in vacuo to obtain the product. The product can be further purified by conventional procedures such as recrystallization, solvent extraction, distillation, chromatography and the like.

In a preferred operation, the N-heterocyclic reactant is added to a stirring mixture of the alkali metal hydride in the solvent and then the phenol or thiophenol reactant is added. After hydrogen evolution ceases, the

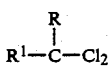

reactant is added and the mixture stirred at the reaction temperature until the reaction is complete. The product is recovered in the manner set forth above.

Method B

Substantially equimolar amounts of a methane compound corresponding to the formula

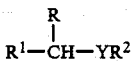

is brominated with a conventional brominating agent such as, for example, N-bromosuccinimide (NBS) in the presence of a solvent and a catalyst. The resulting product is then reacted with a substantially equimolar amount of the N-heterocyclic reactant $HR^3$ in the presence of a solvent and a HB absorber.

The reaction scheme is as follows:

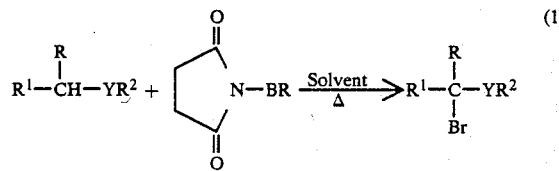

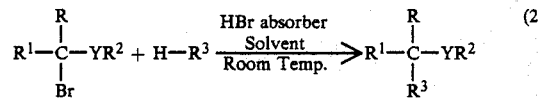

wherein R, $R^1$, $R^2$ and $R^3$ are as hereinabove defined. No attempt has been made to present a balanced equation.

After the completion of the reaction, the reaction mixture is filtered and the solvent removed. The product is then recovered from the residue via preparative high pressure liquid chromatography. If desired the product can be further purified by solvent recrystallization.

In carrying out this reaction, the methane compound is brominated by reacting it with a substantially equimolar amount of a brominating agent such as N-bromosuccinimide in a solvent, such as for example, carbon tetrachloride or chloroform.

Representative HBr absorbers include, for example, sodium or potassium carbonate, triethylamine, 2,6-dimethylpyridine or 1,5-diazabicyclo[3.4.0]nonene-5(DBN).

A catalyst is normally employed in catalytic amounts of from about 0.1 to about 20 mole percent. Representative catalyst include dibenzoylperoxide, ditertiarybutylperoxide or azobis isobutyronitrile.

The reaction is usually carried out under ultraviolet irradiation such as from a conventional sun-lamp. The reaction is initiated by heating the reaction mixture until a vigorous exothermic reaction starts. In a small scale operation, it is convenient to do such heating with a heat gun.

At the completion of the bromination reaction the reaction mixture is immediately cooled to a temperature in the range of from about −10° to about 25° and any insolubles are removed by filtration or other conventional separation procedures. The so recovered mixture is then reacted with the N-heterocyclic reactant in the presence of an HBr absorber such as, for example, sodium, potassium, calcium or lithium carbonate.

This reaction is conveniently carried out at room temperature though temperatures from about −20° to about 75° C. can be employed. At the completion of this reaction, the reaction mixture is filtered to remove any insolubles and then the solvent is removed by evaporation under reduced pressure. The desired product can be recovered from the residue by conventional techniques including preparative high pressure liquid chromatography or solvent recrystallization. If further purification of the product is desired, it may be recrystallized from a solvent such as ethyl ether or pentane or mixtures thereof.

DESCRIPTION OF SOME PREFERRED EMBODIMENTS

In order that the present invention may be more fully understood, the following examples are given primarily by way of illustration and should not be construed as limitations upon the overall scope of the present invention.

Example I 3-((2,4-Dichlorophenoxy)-1H-1,2,4-triazole-1-yl-methyl)pyridine

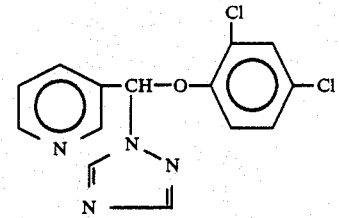

To a stirred mixture of 3.36 grams (g) (0.14 moles (m)) of sodium hydride in 150 milliliter (ml) of dimethylsulfoxide (DMSO) was slowly added 5.18 g (0.075 m) of 1H-1,2,3-triazole and then 11.41 g (0.07 m) of 2,4-dichlorophenol. After hydrogen evolution had ceased, 11.34 g (0.07 m) of 3-(dichloromethyl)pyridine was added thereto and the resulting mixture was stirred at 80°–90° C. for seven (7) hours. The mixture was cooled to room temperature (25° C.) and then poured into 1000 ml of water. The resulting mixture was extracted with ethylether (3 extractions each with 300 ml portions of ether). The extracts were combined and washed with 5 percent (%) aqueous sodium hydroxide, dried over magnesium sulfate and the solvent removed by evaporation under reduced pressure. The residual material was separated by preparative high pressure liquid chromatography using a mixture of 65% hexane and 35% acetone as a solvent. Eluting first was bis-(2,4-dichlorophenoxy)-3-methylpyridine and eluting second was the desired 3-((2,4-dichlorophenoxy)-1H-1,2,4-triazol-1-yl methyl)pyridine which after recrystallization from an ether-hexane mixture gave 6.0 grams of a white solid which melted at 75.5°–78° C. (Compound 1)

Example II 2-((4-Chlorophenoxy)-1H-1,2,4-triazol-1-yl methyl)thiophene

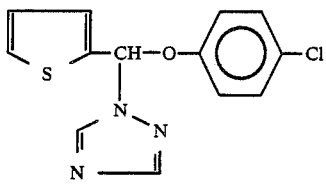

A stirred mixture of 11.23 g (0.05 m) of 2-(4-chlorophenoxy)methyl thiophene and 8.9 g (0.05 m) of N-bromosuccinimide (NBS) in 150 ml of carbon tetrachloride containing a catalytic amount (0.3 g) of benzoylperoxide was irradiated with a sun-lamp and heated with a heat gun until a vigorous exothermic reaction began. Irradiation was continued until all the NBS was used up, ~3–5 minutes. The reaction mixture was immediately cooled to 10° C. in an ice-bath. The mixture was filtered to remove any insolubles. The filtrate was poured into a stirred mixture of 3.45 g (0.05 m) of 1,2,4-triazole and 8.35 g (0.06 m) of powdered potassium carbonate in 300 ml of tetrahydrofuran. The mixture was stirred, at room temperature, for one hour and then filtered and solvent was removed by evaporation under reduced pressure. The residue was purified by preparative high pressure liquid chromatography using a mixture of 80% hexane and 20% acetone as the solvent. The second peak to elute was collected and the solvent was removed therefrom by evaporation under reduced pressure. The desired 2-((4-chlorophenoxy)-1H-1,2,4-triazol-1-yl methyl)thiophene was recovered in a yield of 6.0 g (41% of theoretical). Recrystallization of the product from an ether-pentane mixture and cooling the mixture to minus (−) 20° C. gave colorless needles which melted at 111°–112.5° C. (Compound 2)

By following the procedures as set forth in the above examples, and employing the appropriate reactants, the following compounds in Table I are prepared.

TABLE I
$$R^1-\underset{\underset{R^3}{|}}{\overset{\overset{R}{|}}{C}}-YR^2$$
| Compound No. | R | R¹ | R² | R³ | Y | Physical Data |
|---|---|---|---|---|---|---|
| 3 | H | 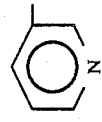 | 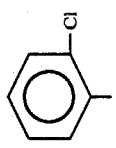 | 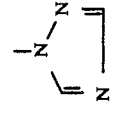 | O | MP 72°–75° C. |
| 4 | H | 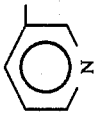 |  | 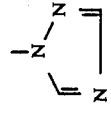 | O | $n_d^{25} = 1.5946$ |
| 5 | H | 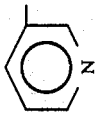 |  | 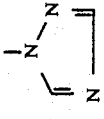 | O | MP 77°–80° C. |
| 6 | H | 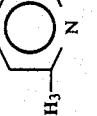 | 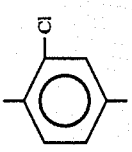 | 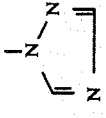 | O | Oil |
| 7 | H | 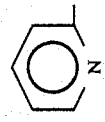 |  | 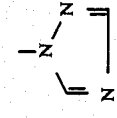 | O | |
| 8 | 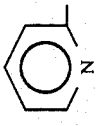 | 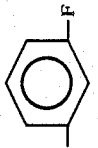 | 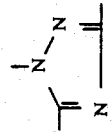 | | S | |

TABLE I-continued $$R^1-\underset{R^3}{\overset{R}{\underset{|}{C}}}-YR^2$$

| Compound No. | R | $R^1$ | $R^2$ | $R^3$ | Y | Physical Data |
|---|---|---|---|---|---|---|
| 9 | H | 2-methylpyridine | 4-Cl-phenyl | 1,2,4-triazole | O | MP 67°–74° C. |
| 10 | H | 2-methylpyridine | 3,4-diCl-phenyl | 1,2,4-triazole | O | MP 93°–94.5° C. |
| 11 | H | 3,6-diCl-pyridine | 3,4-diCl-phenyl | 1,2,4-triazole | O | MP 82°–84° C. |
| 12 | H | 3,6-diCl-pyridine | 4-Cl-phenyl | 1,2,4-triazole | O | Oil |
| 13 | 3,4-diCl-phenyl | 5-NO$_2$-2-NC-pyridine | 3-CF$_3$-4-F-phenyl | 3-C$_4$H$_9$-1,2,4-triazole | S | |
| 14 | 4-C$_4$H$_9$-3-I-phenyl | 2-OCH$_3$-6-Br-pyridine | 2,5-di-OC$_4$H$_9$-phenyl | 3-CH$_3$-5-Br-1,2,4-triazole | S | |
| 15 | H | 3,6-diCl-pyridine | 3,4-diCl-phenyl | 1,2,4-triazole | O | MP 130°–132° C. |

TABLE I-continued $$R^1-\underset{R^3}{\overset{R}{\underset{|}{C}}}-YR^2$$

| Compound No. | R | $R^1$ | $R^2$ | $R^3$ | Y | Physical Data |
|---|---|---|---|---|---|---|
| 16 | H | 3,6-dichloropyridin-2-yl | 4-chlorophenyl | 1,2,4-triazol-1-yl | O | MP 91°–94° C. |
| 17 | H | 6-chloropyridin-2-yl | 3,4-dichlorophenyl | 1,2,4-triazol-1-yl | O | MP 106°–109° C. |
| 18 | H | 6-methylpyridin-2-yl | 4-chlorophenyl | 1,2,4-triazol-1-yl | O | MP 100°–102° C. |
| 19 | 4-methyl-2,6-di(butoxy)pyridin-3-yl | 4-methyl-2,6-di(butoxy)pyridin-3-yl | 4-methyl-2,6-di(butoxy)pyridin-3-yl | 1,2,4-triazol-1-yl | O | |
| 20 | H | 3,5-dichloropyridin-2-yl | 2,4-dichlorophenyl | 1,2,4-triazol-1-yl | O | MP 125.5°–126.5° C. |
| 21 | H | 6-chloropyridin-2-yl | 4-chlorophenyl | 1,2,4-triazol-1-yl | O | tan solid |

TABLE I-continued

R¹—C(R)(R³)—YR²

| Compound No. | R | R¹ | R² | R³ | Y | Physical Data |
|---|---|---|---|---|---|---|
| 22 | H | 2-Cl-pyridyl | 3,4-diCl-phenyl | 1,2,4-triazol-1-yl | O | MP 86°–89° C. |
| 23 | H | 2-Cl-pyridyl | 2,4-diCl-phenyl | 1,2,4-triazol-1-yl | O | MP 95°–98° C. |
| 24 | phenyl | 2-Cl-6-F-pyridyl | 2,4-diF-phenyl | 1,2,4-triazol-1-yl | S | |
| 25 | 4-(n-C₄H₉O)-phenyl | 2-OCH₃-pyridyl | 4-OCH₃-phenyl | 3-C₄H₉-1,2,4-triazol-1-yl | S | |
| 26 | H | 2-Cl-pyridyl | 4-F-phenyl | 1,2,4-triazol-1-yl | O | MP 86.5°–88° C. |
| 27 | H | 2,5-diCl-pyridyl | 2,4-diCl-phenyl | 1,2,4-triazol-1-yl | O | MP 116°–118° C. |
| 28 | H | 2-Cl-pyridyl | 2,4-diCl-phenyl | 1,2,4-triazol-1-yl | O | MP 124°–127° C. |

TABLE I-continued $$R^1-\overset{R}{\underset{R^3}{C}}-YR^2$$

| Compound No. | R | R¹ | R² | R³ | Y | Physical Data |
|---|---|---|---|---|---|---|
| 29 | H | 2-chloropyridin-5-yl | 4-methoxyphenyl | 1,2,4-triazol-1-yl | O | MP 96°–99° C. |
| 30 | H | 4-chlorophenyl | 4-chlorophenyl | 1,2,4-triazol-1-yl | O | MP 161°–163° C. |
| 31 | H | 4-chlorophenyl | 2,4-dichlorophenyl | 1,2,4-triazol-1-yl | O | MP 87°–89° C. |
| 32 | H | 4-chlorophenyl | 2-chlorophenyl | 1,2,4-triazol-1-yl | O | MP 97°–98.5° C. |
| 33 | H | 4-chlorophenyl | 4-iodophenyl | 1,2,4-triazol-1-yl | O | MP 163°–165° C. |
| 34 | H | 4-chlorophenyl | 4-chlorophenyl | imidazol-1-yl | O | MP 119°–121° C. |

TABLE I-continued $$R^1-\underset{\underset{R^3}{|}}{\overset{\overset{R}{|}}{C}}-YR^2$$

| Compound No. | R | $R^1$ | $R^2$ | $R^3$ | Y | Physical Data |
|---|---|---|---|---|---|---|
| 35 | H | 2,4-Cl₂-C₆H₃ | 3,4-Cl₂-C₆H₃ | 1,2,4-triazol-1-yl | O | MP 67°–70° C. |
| 36 | 4-Cl-C₆H₄ | 2,4-Cl₂-C₆H₃ | 4-Cl-C₆H₄ | 1,2,4-triazol-1-yl | S | |
| 37 | 4-C₄H₉O-C₆H₄ | 2,4-Cl₂-C₆H₃ | 3,4-Cl₂-C₆H₃ | 1,2,4-triazol-1-yl | O | MP 84°–87.5° C. |
| 38 | H | 4-H₃CO-C₆H₄ | 2-Br-4-F-C₆H₃ | 3-Cl-1,2,4-triazol-1-yl | S | |
| 39 | 2-H₃C-5-C₄H₉-pyridin-yl | 4-H₃CO-C₆H₄ | 2,4-Cl₂-C₆H₃ | 1,2,4-triazol-1-yl | O | Oil |
| 40 | H | 4-NO₂-3-H₉C₄O-C₆H₃ | 2,5-(CF₃)₂-pyridin-yl | 3-I-1,2,4-triazol-1-yl | S | |
| 41 | H | 4-H₃CO-C₆H₄ | 4-Cl-C₆H₄ | 1,2,4-triazol-1-yl | O | MP 110.5°–112° C. |

TABLE I-continued $$R^1-\underset{R^3}{\overset{R}{C}}-YR^2$$

| Compound No. | R | R¹ | R² | R³ | Y | Physical Data |
|---|---|---|---|---|---|---|
| 42 | H | 4-H₃CO-C₆H₄ | 3,4-Cl₂-C₆H₃ | 1,2,4-triazol-1-yl | O | MP 71°–73° C. |
| 43 | H | 4-H₃CO-C₆H₄ | 2-Cl-pyridin-5-yl | 1,2,4-triazol-1-yl | O | MP 86°–88° C. |
| 44 | C₆H₅ | C₆H₅ | 4-Cl-C₆H₄ | 1,2,4-triazol-1-yl | O | MP 108°–109.5° C. |
| 45 | C₆H₅ | C₆H₅ | 3,4-Cl₂-C₆H₃ | 1,2,4-triazol-1-yl | O | MP 87.5°–89.5° C. |
| 46 | 3,4-Cl₂-C₆H₃ | C₆H₅ | 4-NO₂-C₆H₄ | 1,2,4-triazol-1-yl | S | |
| 47 | 4-H₃C-C₆H₄ | 2-CF₃-C₆H₄ | 4-Cl-C₆H₄ | 1,2,4-triazol-1-yl | O | |

TABLE I-continued $$R^1-\underset{R^3}{\overset{R}{\underset{|}{C}}}-YR^2$$

| Compound No. | R | R¹ | R² | R³ | Y | Physical Data |
|---|---|---|---|---|---|---|
| 48 | 4-NO₂-phenyl | phenyl | 3-Cl-5-OC₄H₉-pyridin-2-yl | 1,2,4-triazol-1-yl | O | |
| 49 | phenyl | 2,6-Cl₂-pyridin-4-yl | 5-CN-pyridin-2-yl | 2-C₄H₉-imidazol-1-yl | S | |
| 50 | 4-Cl-phenyl | 4-CH₃-phenyl | 4-Cl-phenyl | 1,2,4-triazol-1-yl | O | Gum |
| 51 | 4-C₂H₅-phenyl | 5-CF₃-thien-2-yl | 2,4-(CH₃)₂-phenyl | 5-Cl-1,2,4-triazol-1-yl | S | |
| 52 | 4-C₃H₇-phenyl | 3,4-Cl₂-thien-2-yl | pyridin-2-yl | 3,5-(CH₃)₂-pyrazol-1-yl | S | |
| 53 | H | 5-CH₃-thien-2-yl | pyridin-4-yl | 4,5-Cl₂-imidazol-1-yl | O | |

TABLE I-continued $$R^1-\underset{R^3}{\overset{R}{\underset{|}{C}}}-YR^2$$

| Compound No. | R | $R^1$ | $R^2$ | $R^3$ | Y | Physical Data |
|---|---|---|---|---|---|---|
| 54 | pyridyl | 2-butoxy-thienyl | pyridyl | 3,5-dichloropyrazolyl | O | |
| 55 | H | pyridyl | 4-chlorophenyl | 3-chloropyrazolyl (fused) | O | |
| 56 | pyridyl | 3-methyl-5-methylthienyl | phenyl | 5-chloro-1,2,4-triazolyl | O | |
| 57 | H | pyridyl | 3,5-dichlorophenyl | triazolyl | O | |
| 58 | H | pyridyl | 3,4-dichlorophenyl | triazolyl | O | |
| 59 | H | pyridyl | 3,5-dichlorophenyl | triazolyl | O | |

TABLE I-continued
$$R^1-\underset{R^3}{\overset{R}{\underset{|}{C}}}-YR^2$$
| Compound No. | R | R¹ | R² | R³ | Y | Physical Data |
|---|---|---|---|---|---|---|
| 60 | H |  (pyridyl) |  (2,4-dichlorophenyl) |  (1,2,4-triazolyl) | O | |
| 61 | H |  (4-chlorophenyl) |  (4-iodophenyl) |  (1,2,4-triazolyl) | O | |

Preparation of Starting Materials

The dihalomethyl compounds corresponding to the formula

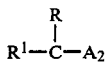

wherein R and R$^1$ are as hereinbefore defined and A is chloro or bromo and which are employed as starting materials, are known compounds and can be prepared by a variety of procedures.

In one such procedure for preparing compounds wherein A is bromine, one mole of an appropriate aromatic methyl compound of the formula

is reacted with 2 moles of a brominating agent such as N-bromosuccinimide (NBS) in the presence of a catalyst and a solvent. This reaction can be carried out employing the same procedures and conditions as set forth for step 1 of Method B.

Example III

4-Chloro-α,α-dibromotoluene

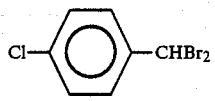

A mixture of 25.32 g (0.2 m) of 4-chlorotoluene, 71.2 g (0.4 m) of NBS, 1.0 g of benzoylperoxide and 700 ml of carbon tetrachloride was heated at reflux until all the NBS had been consumed (~3-4 hours). Analysis showed the mixture to be composed of mono, di and tribrominated material. An additional 15.0 g of NBS was added and heating was continued until it was consumed. Analysis indicated the product to contain ~7 percent monobrominated material, ~14 percent tribrominated material and the desired dibrominated material. The mixture was distilled through a 5-plate Oldershaw column to give 25 g (44 percent of theoretical) of the desired 4-chloro-α,α-dibromotoluene which boiled at 64°-66° C. at 0.01 millimeter of mercury.

Those compounds wherein R and R$^1$ are both phenyl are known compounds as taught in U.S. Pat. No. 3,755,345 or those compounds which are unknown can be prepared employing analogous methods.

Those compounds wherein R is hydrogen and R$^1$ is pyridyl are known compounds and can be prepared as taught in U.S. Pat. No. 4,260,766 and the patents cited therein. The pyridine compounds which are substituted with nitro or trifluoromethyl groups can be prepared as indicated above employing the appropriate starting materials.

The bromomethyl compounds corresponding to the formula

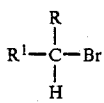

wherein R and R$^1$ are as hereinbefore defined and which are employed as starting materials, are known compounds and can be prepared by a variety of procedures.

The arylmethyl compounds corresponding to the formula

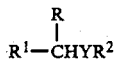

can be prepared by the reaction of substantially equimolar amounts of a bromomethyl compound of the formula

and a phenol, thiophenol, pyridinol or thiopyridinol corresponding to the formula

in the presence of a solvent and an HBr absorber.

The reaction scheme is as follows:

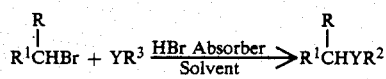

wherein R, R$^1$, R$^2$ and Y are as hereinbefore defined. No attempt has been made to present a balanced equation.

In carrying out this reaction, the reactants are mixed together in any suitable fashion. Preferably, the phenol reactant is employed in slight excess to insure completion of the reaction. Representative solvents include, acetonitrile, acetone, DMF, or DMSO. Representative HBr absorbers include sodium and potassium carbonate, triethylamine, 2,6-dimethylpyridine or DBN. The reaction mixture is stirred and heated at reflux for about 15 minutes to about 6 hours. At the completion of the reaction, the solvent is removed and the residue diluted with water. The mixture is extracted with a solvent such as methyl ether, methylene chloride, chloroform or toluene. The organic extract is washed with a dilute sodium hydroxide solution followed by water and a saturated sodium chloride solution and then dried. The product can be recovered by distillation and can be further purified, if desired, by solvent recrystallization.

Example IV (4-Chlorophenoxy)methyl thiophene

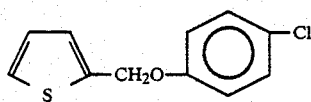

To a solution of 51.75 g (0.29 m) of 2-bromomethylthiophene and 38.6 g (0.3 m) of 4-chlorophenol in 400 ml of acetonitrile was added, all at once, 38.6 g of powdered potassium carbonate. The resulting mixture was stirred and heated at reflux for one (1) hour. The solvent was removed by evaporation under reduced pressure and 400 ml of water was added to the residue. The resulting aqueous mixture was extracted three times with 200 ml portions of ether. The organic extracts were combined and then washed sequentially with 50 ml of a 10 percent sodium hydroxide solution, 300 ml of water and 300 ml of a saturated sodium chloride solution. The extracts were dried over magnesium sulfate and the solvent removed by evaporation under reduced pressure. The residue was an orange oil which slowly solidified upon standing. Distillation of the residue gave a main fraction boiling at 96°–100° C. at 0.01 millimeter of mercury. The crude product slowly crystallized and was purified by recrystallization from hexane. The (4-chlorophenoxy)methylthiopene product, a white solid, was recovered in a yield of 41 g (63 percent of theoretical) and melted at 45°–47° C.

The Examples set forth above under the "Preparation of Starting Materials" heading are given only as illustrations of the various preparations which can be employed and should not be considered as limiting.

The compounds of the present invention are useful as pesticides and are particularly effective for the kill of certain plants and the kill and control of various plant fungal organisms and certain insect pests. In addition many of the compounds have been found to have plant growth regulation activity. In this latter capacity, plants may be stunted or their growth can increase.

In their use a pesticidal or pesticidally effective amount or a growth regulatory effective amount of the active compound per se or a composition incorporating said amount of the compound in admixture with a suitable inert carrier or adjuvant is used as the toxicant for contact with the pest, its habitat or with the desired plants. The pesticidal amount, of course, is that quantity which elicits toxic mortality among the treated pests or which regulates the growth of the plants. Generally, such responses result by contacting the target pests, their habitat or the desired plants with a composition containing from 0.00001 to 99 or more percent of the active compound in the total composition. Good results are achieved upon contact with a composition containing about 1000 parts of the active compound per million by weight.

Suitable compositions include those which are in the form of liquid solutions, liquid emulsifiable concentrates, and dust or granular preparations. Such can be further diluted as and where appropriate with convention diluents.

Liquid compositions containing the active compound are prepared by dissolving the active compound in a suitable inert organic solvent such as acetone, toluene, xylene, methylene chloride, chlorobenzene, ethyl ether or petroleum distillates, or other liquid carriers, propellant substances or by dispersing the active compound in water with or without the aid of a suitable surface acting dispersing agent such as can be provided by ionic or nonionic dispersing and emulsifying agents.

The aqueous compositions may contain one or more water-immiscible solvents for the active compounds. In such compositions, the carrier comprises an aqueous emulsion, that is, a mixture of water-immiscible solvent, emulsifying agent and water. The choice of dispersing and/or emulsifying agent and the amounts thereof employed is dictated by the nature of the composition type and by the ability of the agent to facilitate the dispersion of the active compound in the aqueous carrier to produce the desired composition. Dispersing and emulsifying agents which may be employed in the compositions include the condensation products of alkylene oxides with phenols and organic acids, alkylarylsulfonates, polyoxyethylene derivatives or sorbitan esters, complex ether alcohols, mahogany soaps, and the like. In such compositions, the surface active agents are usually employed in the amount of from 1 to 20 percent by weight of the combined weight of the surface active agent and the active compound.

In the preparation of dust compositions, the active compound is dispersed in and on a finely divided inert solid such as talcum, chalk, gypsum, and the like. In such operations, the carriers are mechanically ground with the compounds or wet with a volatile organic solvent solution thereof. Similarly, dust compositions containing the compound may be prepared from bentonite, fuller's earth, attapulgite, and other clays. Depending upon the proportions of ingredients, these dust compositions may be employed as concentrates and subsequently diluted with additional solid surface acting dispersing agent or with talc, chalk, or gypsum and the like to obtain a desired amount of active agent in a composition adapted to be applied for pest control. Also, such concentrate dust compositions may be dispersed in water with or without the aid of a dispersing agent to form spray mixtures.

Granular formulations are conveniently prepared by impregnations, such as through simple mechanical mixing, of the active compound in a presized carrier, usually of the type hereinbefore set forth.

In practice, the active compound is distributed so as to provide contact of the target pest or plants with effective amounts of the active compound. Such contact can be achieved through direct contact with the active compound or by more indirect means such as by application to the habitat. Thus, for example, the active compound hereof or a composition thereof can be spread throughout the environs of the target host so as to both provide direct and indirect contact thereof with a toxic or pesticidally effective amount or plant growth regulatory amount of the active compound or a composition containing said active compound so as to provide ultimate contact therewith.

Example V

Aqueous compositions (dispersions) of various azolomethanes were prepared by admixing one of the active ingredients, dissolved in a suitable solvent, with a predetermined amount of a surfactant to give aqueous dispersions containing various predetermined amounts of one of the compounds as the sole active toxicant.

These compositions were evaluated, as insecticides, for the control of two-spotted spider mites, beet armyworm larvae, tobacco budworm larvae, tobacco budworm eggs (ovicidal effect), codling moth, peach aphid and leaf hoppers wherein the azolomethane was present in the composition in an amount of 400 parts of the compound per million parts of ultimate composition (ppm); and for Western spotted cucumber beetle and black cut worms wherein the azolomethane present in an amount of 25 parts of the compound per million parts of the ultimate composition (ppm).

Test procedures were employed as follows:

Two-Spotted Spider Mites

Separate wild mustard plants were infested with 20 two-spotted spider mites and the plants were sprayed with one of the dispersions to run off. In a like manner, 20 two-spotted spider mites were placed on control plants and the plants sprayed to run off with a solution containing only water and surfactant. The plants were maintained under conditions conducive to the growth of the plants and mites. After a period of two days, the plants were examined to determine the percent kill and control of the mites.

Western Spotted Cucumber Beetle

Seventy-five grams of air-dried soil was placed in an 8-ounce container. To the soil was added sufficient volume of the above 400 ppm aqueous dispersion, to give various predetermined concentrations of the active ingredient in the soil on a soil-chemical basis. The treated soil was air-dried and thoroughly mixed. To each treated container, and control containers treated with water and surfactant alone, was added 0.5 milliliter of an aqueous suspension of the eggs of the Western spotted cucumber beetle (WSCB) (70–80 eggs, 3–4 days old). Additional treated soil was used to cover the eggs and a sprouted corn seed was placed on the soil and covered with additional treated soil. The containers were thereafter maintained under conditions conducive to the growth of the seeds and the hatching of the eggs (75°–80° F.) Ten to twelve days after treatment, the containers and the plants therein were examined to determine the percent kill and control of the larvae from the hatched eggs.

Beet Armyworm

Separate cotton plant leaves were thoroughly wetted briefly by dipping into one of the dispersions and the wetted leaves placed in an open Petri dish and permitted to dry. After the leaves were dry, 5 live armyworm larvae, approximately late second instar were placed in each Petri dish. In identical operations, 5 live and late second instar beet armyworm larvae were placed in control Petri dishes, the leaf therein having been wetted with a solution containing only water and surfactant. The dishes were maintained under moist conditions conducive for the growth of the beet armyworm larvae for a period of about 5 days. At the end of the 5-day period, the dishes were examined to determine the percent kill and control of the beet armyworm larvae.

Tobacco Budworm

Separate 3-inch disc cut from tobacco plant leaves were thoroughly wetted briefly by dipping into one of the dispersions and the wetted leaves placed in an open Petri dish and permitted to dry. After the leaves were dry, 5 live tobacco budworm larvae approximately late second instar were placed in each Petri dish. In identical operations, 5 live tobacco budworm larvae were placed in control Petri dishes, the leaf therein having been wetted with a solution containing only water and surfactant. The dishes were maintained under moist conditions and at 80° F. conducive for the growth of the tobacco budworm larvae for a period of about 2 days. At the end of the 2-day period, the dishes were examined to determine the kill and control of the tobacco budworm larvae.

Codling Moth

Sheets containing egg masses of codling moths were pinned to apples and the egg sheets and apples were drenched with one of the aqueous dispersions. Separate egg masses and apples were also treated with a control mixture containing only water and surfactant. The egg masses/apples were incubated under conditions conducive to the hatching of the eggs and the growth of the larvae therefrom. Ten days after treatment, the apples were examined for the presence of egg hatch and larvae. Counts of the number of larval penetration in the treated fruit were compared to the number present in the untreated control to determine the percent control obtained with the test compounds.

Peach Aphid

Separate chili pepper plants were infested with 20 green peach aphids and the plants sprayed with one of the dispersions to run off. In a like manner, 20 green peach aphids were placed on control plants and the plants sprayed to run off with a solution containing only water and surfactant. The plants were maintained under conditions conducive to the growth of the plants and aphids. After a period of two days, the plants were examined to determine the percent kill and control of the green peach aphids.

In such test, it was determined that each of compounds 5, 59 and 60 gave at least 50 percent kill and control of two-spotted spider mites; each of compounds 31 and 58 gave 100 percent kill and control of black cut worms; compound 58 was found to give 100 percent kill and control of beet armyworm larvae; compound 41 was found to give 100 percent kill and control of codling moth larvae; each of compounds 2, 7, 34, 57 and 59 were found to give at least 75 percent kill and control of peach aphids; and each of compounds 10, 31 and 44 were found to give at least 50 percent kill and control of leaf hoppers.

Example VI

Aqueous compositions of various azolomethanes were prepared by admixing one of the active ingredients, dissolved in a suitable solvent, with a predetermined amount of a surfactant to give aqueous dispersions containing various predetermined amounts of one of the compounds, as the sole active toxicant.

These compositions were evaluated for pre-emergent applications on plots immediately after they were seeded with crabgrass, morning glory, barnyard grass, cotton, pigweed, yellow foxtail and velvet leaf. Other plots similarly seeded with the above plant species were treated with the like compositions containing no toxicant to serve as control plots. The treating applications were carried out by drenching the soil with the aqueous compositions to obtain a treating rate of 10.0 pounds per acre. Thereafter, the plots were maintained under conditions conducive for good plant growth. Two weeks after treatment, the plots were examined to determine the percent plant growth and evaluated. The results of the examinations are set forth below.

In such test, it was determined that each of compounds 5, 9, 10, 17, 21, 29, 34, 39, 55 and 60 were found to give at least 50 percent kill and control of undesired cotton plants; each of compounds 2, 3, 7, 9, 17, 18, 20, 21, 29, 34, 37, 39, 55 and 60 were found to give at least 50 percent kill and control of pigweed plants; each of compounds 7, 12, 16, 17, 18, 20, 34, 55, 58, 59 and 60 were found to give at least 60 percent kill and control of crabgrass plants; each of compounds 4, 12, 16, 17, 18, 20, 34, 55, 58, 59 and 60 were found to give at least 50 percent kill and control of yellow foxtail plants; each of the compounds 7, 9, 10, 17, 20, 34, 37, 39, 44, 55, 58, 59 and 60 were found to give at least 50 percent kill and control of morning glory plants; each of the compounds 3, 7, 9, 10, 17, 20, 33, 34, 37, 39, 59 and 60 were found to give at least 50 percent kill and control of velvet leaf plants; and each of compounds 7, 18, 20, 45, 55 and 59 were found to give at least 60 percent kill and control of barnyard grass plants.

Example VII

Aqueous compositions (dispersions) of various azolomethanes were prepared by admixing one of the active ingredients, dissolved in a suitable solvent, with a predetermined amount of surfactant to give aqueous dispersions containing various predetermined amounts of one of the compounds, as the sole active toxicant.

These compositions were evaluated for post-emergent control of barnyard grass, crabgrass, pigweed, yellow foxtail, cotton, morning glory and velvet leaf. In these evaluations, plots of the above plant species grown to a height of about 4 inches were used. Aqueous spray compositions, each containing 4,000 parts of given aryl(aryloxy)azolmethane compound per million parts of ultimate composition, were prepared and each separate composition was applied to a separate plot. The application was made to the point of run-off and was carried out with conventinal spraying equipment. Other plots were sprayed with similar compositions containing no toxicant to serve as controls. Thereafter, the plots were maintained under conditions conducive for plant growth. Two weeks after treatment, the plots were examined for plant growth and evaluated.

In such tests, it was determined that each of compounds 5, 9, 10, 17, 21, 28, 34, 39 and 70 were found to give at least 60 percent kill and control of cotton plants; each of compounds 3, 7, 9, 17, 18, 20, 21, 28, 34, 37, 55 and 60 were found to give at least 60 percent kill and control of pigweed plants; each of compounds 5, 7, 12, 16, 17, 18, 20, 34, 55, 58, 59 and 60 were found to give at least 70 percent kill and control of crabgrass plants; each of compounds 4, 12, 16, 17, 18, 20, 34, 55, 58, 59 and 60 were found to give at least 50 percent kill and control of yellow foxtail plants; each of compounds 5, 7, 9, 10, 17, 18, 34, 37, 39, 44, 55, 58, 59 and 60 were found to give at least 50 percent kill and control of morning glory plants; each of compounds 3, 5, 7, 9, 10, 17, 20, 33, 34, 37, 39, 59 and 60 gave at least 50 percent kill and control of velvet leaf plants; and each of compounds 7, 18, 20, 45, 58 and 59 gave at least 60 percent kill and control of barnyard grass plants.

Example VIII

Aqueous compositions (dispersions) of various azolomethanes were prepared by admixing one of the active ingredients, dissolved in a suitable solvent, with a predetermined amount of a surfactant to give aqueous dispersions containing various predetermined amounts of one of the compounds as the sole active toxicant.

The compositions were evaluated, as fungicides, for the control of grape downy mildew and apple powdery mildew wherein the azolomethane was present in the composition in an amount of 500 ppm; for the control of apple scab wherein the azolomethane was present in an amount of 400 ppm; for Verticillium wilt wherein the azolomethane was present in an amount of 100 ppm; and for tobacco black shank and tobacco black root rot wherein the azolomethane was present in an amount of 25 ppm.

Test procedures were employed as follows:

Tobacco Black Shank

Soil infected with the tobacco black shank pathogen *Phytophthora parasitica* var. *nicotianeae* was uniformly mixed and placed in 6-inch pots. To said pots were transplanted six week old tobacco seedlings of the "402" variety which has been grown in pathogen free soil. The test dispersions were employed to treat separate pots containing the seedling by pouring 100 cubic centimeters of each of the test dispersions onto the soil, assuring root contact with sufficient chemical. Additional pots were treated with an aqueous acetone solution containing no toxicant to serve as controls. After treatments, the plants were maintained under conditions conducive for good plant growth. Nineteen days after treatment, the plants were examined for disease control.

Apple Powdery Mildew

The test compositions were drenched onto soil in which apple plant seedlings were growing. One week later, the plant foliage was sprayed with a suspension of spores of apple powdery mildew (*Podosphaera leucotricha*). When disease symptoms on control plants developed, evaluation of percent control on plants in treated pots was made.

Apple Scab

The foliage of apple tree seedlings was sprayed to run off with solutions of compounds of the invention prepared as described above. Four days after the treatment, the plants were inoculated with spores of *Venturia inaequalis*. One week after the inoculation, the percent control of apple scab disease was determined.

Tobacco Black Root Rot

Tobacco plant seedlings were transplanted into 2-inch (5 cm) diameter pots containing soil infested with tobacco black root rot (*Thielaviopsis basicola*). Immediately after transplanting, the pots were drenched with 40 ml of one of the test dispersions, two pots per dilution. Control pots were drenched with acetone solution containing no test compound. The pots were maintained at a temperature of 60° F. and (15.5° C.) and watered daily. The test was evaluated by estimating the percentage of root system that was injured, the evaluation being made when roots of plants in the control pots showed 98 percent injury.

Grape Downy Mildew

The underside of the leaves of grape seedlings (cv. Carignane) at the 3–4 leaf stage were sprayed with an aqueous suspension of the test material. After application, the underside of the plant leaves were sprayed with a spore suspension of *Plasmorpara viticola* in distilled water. The plants were held in an infection chamber at 20° to 22° C. and 100% r.h. for 7–8 days. When the disease symptoms were well developed, the seedlings were graded for disease control by rating seedlings, treated with the above solution (suspension) less toxicants, as 'no control' and treated plants with the absence of disease symptoms as '100% control'.

Verticillium Wilt

Soil infected with the vascular wilt organism Verticillium albo-atrum was uniformly mixed and used to fill 6-inch pots to within 3½ inches from the top. The pots were treated with aqueous dispersions of the test compound. Additional infected soil was added to the pots to within 1¼ inch of the top. Five cotton seeds were planted in each pot and the pots were watered lightly. Sterile soil was added to the pots to cover the seeds. Additional pots were also prepared as above except they were not treated with chemical to serve as controls. The pots were thereafter maintained under conditions conducive to good plant growth. Eight weeks after treatment, the pots were examined to determine the percent of disease control.

In such test, it was determined that each of compounds 2, 3, 5, 6, 7, 9, 10, 11, 12, 15, 17, 20, 21, 28, 29, 31, 42, 43, 57 and 60 were found to give at least 50 percent kill and control of causative organisms of barley powdery mildew; each of compounds 2, 7, 21, 28, 29, 33, 34 and 57 were found to give at least 75 percent kill and control of the causative organism of wheat leaf rust; each of compounds 4, 5, 6, 20, 21, 29, 30, 43, 57 and 58 were found to give 100 percent kill and control of the causative organism of verticillium wilt; each of compounds 2, 7, 15, 34, 42, 44, 57 and 61 were found to give at least 50 percent kill and control of the causative organism of grape downy mildew; each of compounds 3, 7, 12, 15, 16, 21, 30, 31, 32, 39, 41, 57 and 60 were found to give at least 75 percent kill and control of the causative organism of apple scab; each of compounds 2, 3, 5, 6, 7, 9, 10, 11, 12, 15, 17, 18, 21, 31, 35, 37, 39, 42, 43, 44, 45, 57, 58, 59 and 60 were found to give at least 50 percent kill and control of the causative organism of apple powdery mildew; and each of compounds 2, 3, 4, 5, 18, 44, 60 and 61 were found to give 100 percent kill and control of the causative organism of tobacco black root rot.

Example IX

Tests were conducted to determine the effectiveness of the test compositions in increasing the growth enhancement as evidenced by an increase in the dry weight of the roots of sugar beets.

Sugar beets were grown in a greenhouse in pots whose soil consisted of ~97 percent sand. When the plants were 21 days old, they were sprayed to the point of run-off with various dilutions of aqueous solutions of the test compositions. These solutions were prepared by dissolving a predetermined amount of one of the test compounds in a predetermined amount of water containing 0.1 percent of a wetting agent. Untreated plants were maintained as controls.

One month after treatment, the plants were removed from the soil and the roots removed from the plants. The roots were placed in a forced air oven at 60° C. until no moisture remained (48-72 hours). The dry weight of the roots were measured and the results calculated as a percent of the control.

TABLE II

| Compound | Increase in dry weight of sugar beet roots as a percent of control dosage in PPM | | |
|---|---|---|---|
| | 6 | 25 | 100 |
| 16 | 14 | N.A.* | 13 |
| 42 | 46 | 25 | 26 |
| 45 | 27 | 31 | 14 |

*N.A. = No increase in dry weight noted.

Example X

Tests were conducted to determine the effectiveness of the test compositions in regulating the growth of sugar beet plants as evidenced by the stunting of the plants.

Sugar beets were grown in a greenhouse in pots whose soil, consisted of ~97 percent sand. When the plants were 21 days old, they were sprayed to the point of run-off with various dilutions of aqueous solutions of the test compositions. These solutions were prepared by dissolving a predetermined amount of one of the test compounds in a predetermined amount of water containing 0.1 percent of a wetting agent. Untreated plants were maintained as controls.

One month after treatment, the plants were examined to determine the degree of stunting which occurred. Stunting of sugar beet plants was based on whether at least a 20 percent reduction occurred in the length of the stem which holds the leaf and in the leaf area. The compounds were rated as having a stunting activity index of 1 if the treated plants were stunted at a treating dosage rate of 165 ppm; a stunting activity index of 2 if the treated plants were stunted at a treating dosage of between 165 and 330 ppm and a stunting activity index of 3 if the treated plants were stunted at a treating dosage of between 330 and 1000 ppm. In these tests, compounds 9, 16, 44, 45 and 57 were found to have a stunting activity of 1; compounds 1, 5, 7, 10, 11, 12, 17, 21, 41, 42, 58 and 59 were found to have a stunting activity of 2 and compounds 3, 4, 6, 15, 20, 31, 32, 33, 35, 39 and 43 were found to have a stunting activity of 3.

What is claimed is:

1. A compound corresponding to the formula

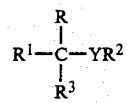

wherein

R represents pyridyl or pyridyl substituted independently with from 1 to 3 bromo, chloro, fluoro, iodo, $C_1$-$C_4$ alkyl, $C_1$-$C_4$ alkoxy, $NO_2$, CN or $CF_3$ groups;

$R^1$ represents thienyl or thienyl substituted independently with from 1 to 3 bromo, chloro, fluoro, iodo, $C_1$-$C_4$ alkyl, $C_1$-$C_4$ alkoxy, $NO_2$, CN or $CF_3$ groups;

$R^2$ represents phenyl or phenyl substituted independently with from 1 to 3 bromo, chloro, fluoro, iodo, $C_1$-$C_4$ alkyl, $C_1$-$C_4$ alkoxy, $NO_2$, CN or $CF_3$ groups;

$R^3$ represents a 5-membered N-heterocyclic ring of the formula

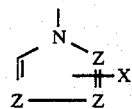

wherein each Z independently represents —CH or N and at least one of Z is N;

X is $C_1$-$C_4$ alkyl, Br, Cl, F or I and n represents an integer of from 0 to 3 and Y is oxygen or sulfur.

2. A pesticidal composition which comprises an inert adjuvant in admixture with a pesticidally effective amount of a compound corresponding to the formula

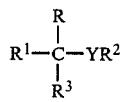

wherein
- R represents pyridyl or pyridyl substituted independently with from 1 to 3 bromo, chloro, fluoro, iodo, $C_1$-$C_4$ alkyl, $C_1$-$C_4$ alkoxy, $NO_2$, CN or $CF_3$ groups;
- $R^1$ represents thienyl or thienyl substituted independently with from 1 to 3 bromo, chloro, fluoro, iodo, $C_1$-$C_4$ alkyl, $C_1$-$C_4$ alkoxy, $NO_2$, CN or $CF_3$ groups;
- $R^2$ represents phenyl or phenyl substituted independently with from 1 to 3 bromo, chloro, fluoro, iodo, $C_1$-$C_4$ alkyl, $C_1$-$C_4$ alkoxy, $NO_2$, CN or $CF_3$ groups;
- $R^3$ represents a 5-membered N-heterocyclic ring of the formula

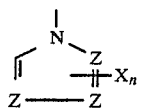

wherein
- each Z independently represents —CH or N and at least one of Z is N;
- X is $C_1$-$C_4$ alkyl, Br, Cl, F or I and
- n represents an integer of from 0 to 3 and
- Y is oxygen or sulfur.

3. A method for the kill and control of fungal or insect pest which comprises contacting said pest with a pesticidally effective amount of a composition which comprises an inert adjuvant in admixture with a compound corresponding to the formula

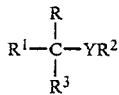

wherein
- R represents pyridyl or pyridyl substituted independently with from 1 to 3 bromo, chloro, fluoro, iodo, $C_1$-$C_4$ alkyl, $C_1$-$C_4$ alkoxy, $NO_2$, CN or $CF_3$ groups;
- $R^1$ represents thienyl or thienyl substituted independently with from 1 to 3 bromo, chloro, fluoro, iodo, $C_1$-$C_4$ alkyl, $C_1$-$C_4$ alkoxy, $NO_2$, CN or $CF_3$ groups;
- $R^2$ represents phenyl or phenyl substituted independently with from 1 to 3 bromo, chloro, fluoro, iodo, $C_1$-$C_4$ alkyl, $C_1$-$C_4$ alkoxy, $NO_2$, CN or $CF_3$ groups;
- $R^3$ represents a 5-membered N-heterocyclic ring of the formula

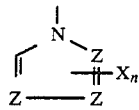

wherein
- each Z independently represents —CH or N and at least one of Z is N;
- X is $C_1$-$C_4$ alkyl, Br, Cl, F or I and
- n represents an integer of from 0 to 3 and
- Y is oxygen or sulfur.

4. A method for regulating the growth of plants which comprises contacting said plants with a plant growth regulating amount of a composition which comprises an inert adjuvant in admixture with a compound corresponding to the formula

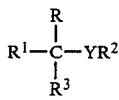

wherein
- R represents pyridyl or pyridyl substituted independently with from 1 to 3 bromo, chloro, fluoro, iodo, $C_1$-$C_4$ alkyl, $C_1$-$C_4$ alkoxy, $NO_2$, CN or $CF_3$ groups;
- $R^1$ represents thienyl or thienyl substituted independently with from 1 to 3 bromo, chloro, fluoro, iodo, $C_1$-$C_4$ alkyl, $C_1$-$C_4$ alkoxy, $NO_2$, CN or $CF_3$ groups;
- $R^2$ represents phenyl or phenyl substituted independently with from 1 to 3 bromo, chloro, fluoro, iodo, $C_1$-$C_4$ alkyl, $C_1$-$C_4$ alkoxy, $NO_2$, CN or $CF_3$ groups;
- $R^3$ represents a 5-membered N-heterocyclic ring of the formula

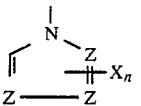

wherein
- each Z independently represents —CH or N and at least one of Z is N;
- X is $C_1$-$C_4$ alkyl, Br, Cl, F or I and
- n represents an integer of from 0 to 3 and
- Y is oxygen or sulfur.

* * * * *